United States Patent [19]

Prem et al.

[11] Patent Number: 5,630,836
[45] Date of Patent: May 20, 1997

[54] TRANSCUTANEOUS ENERGY AND INFORMATION TRANSMISSION APPARATUS

[75] Inventors: Edward K. Prem, Allison Park; David E. Cuervo, McMurray, both of Pa.

[73] Assignee: Vascor, Inc., Pittsburgh, Pa.

[21] Appl. No.: 375,357

[22] Filed: Jan. 19, 1995

[51] Int. Cl.⁶ .............................. A61B 17/36; A61N 1/37
[52] U.S. Cl. .................................. 607/61; 607/60; 607/62; 607/66; 607/2; 607/1
[58] Field of Search .............................. 607/1, 2, 60, 61, 607/62, 66

[56] References Cited

U.S. PATENT DOCUMENTS

| | | |
|---|---|---|
| 3,195,540 | 7/1965 | Waller . |
| 3,942,535 | 3/1976 | Schulman . |
| 4,143,661 | 3/1979 | LaForge et al. . |
| 4,275,739 | 6/1981 | Fischell . |
| 4,384,829 | 5/1983 | Conley et al. . |
| 4,457,673 | 7/1984 | Conley et al. . |
| 4,548,208 | 10/1985 | Niemi . |
| 4,665,896 | 5/1987 | LaForge et al. . |
| 4,679,560 | 7/1987 | Galbraith .................................. 607/60 |
| 5,314,457 | 5/1994 | Jeutter et al. .............................. 607/60 |

FOREIGN PATENT DOCUMENTS 2007439  7/1991  Canada .

OTHER PUBLICATIONS

"A Completely Implanted Left Ventricular Assist Device" by W. Weiss, G. Rosenberg, A. Synder, J. Donachy, Sr., J. Reibson, O. Kawaguchi, J. Sapirstein, W. Pae, W. Pierce, ASAIO Journal, 1993.

"Research and Development Systems for Transmitting Energy Through Intact Skin" by C. Sherman, B. Daly, K. Dasse, W. Clay, M. Szycher, J. Handrahan, J. Schuder, M. Lewis, M. Worthington, R. Hopkins, V. Poirier Thermo Electron Corporation, Jul. 1983.

*Primary Examiner*—Lee S. Cohen
*Assistant Examiner*—Stephen Huang
*Attorney, Agent, or Firm*—Buchanan Ingersoll, P.C.

[57] ABSTRACT

An apparatus for transcutaneously transmitting power and communication signals to an implantable device. The apparatus can include generators for power and information signals; receivers; and a coupler for independently coupling the power signal and a first information signal. An internal unit can have receivers for power and information signals; a second signal generator; and an independent coupler. The first and second information signal can be transmitted at a frequency greater than the power frequency. The external unit can also include a signal conditioner for symmetrically transceiving the first and second information signals; and an external data controller for symmetrically controlling the information signals. The internal unit can also include a voltage regulator converter; an internal signal conditioner for symmetrically transceiving the information signals; and a data controller. Symmetrically controlling can include ASK modulation of a data signal upon an RF carrier signal.

44 Claims, 9 Drawing Sheets

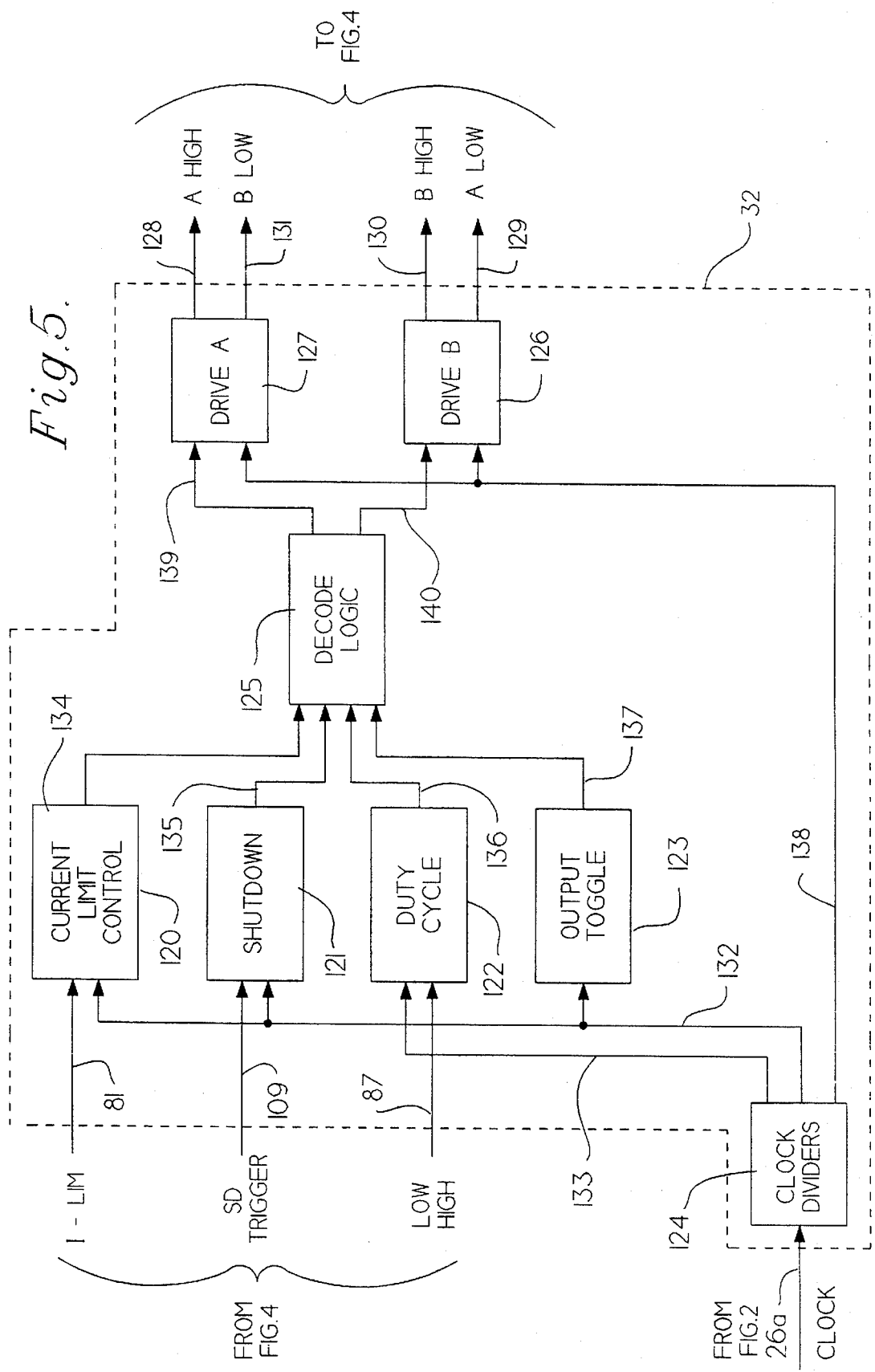

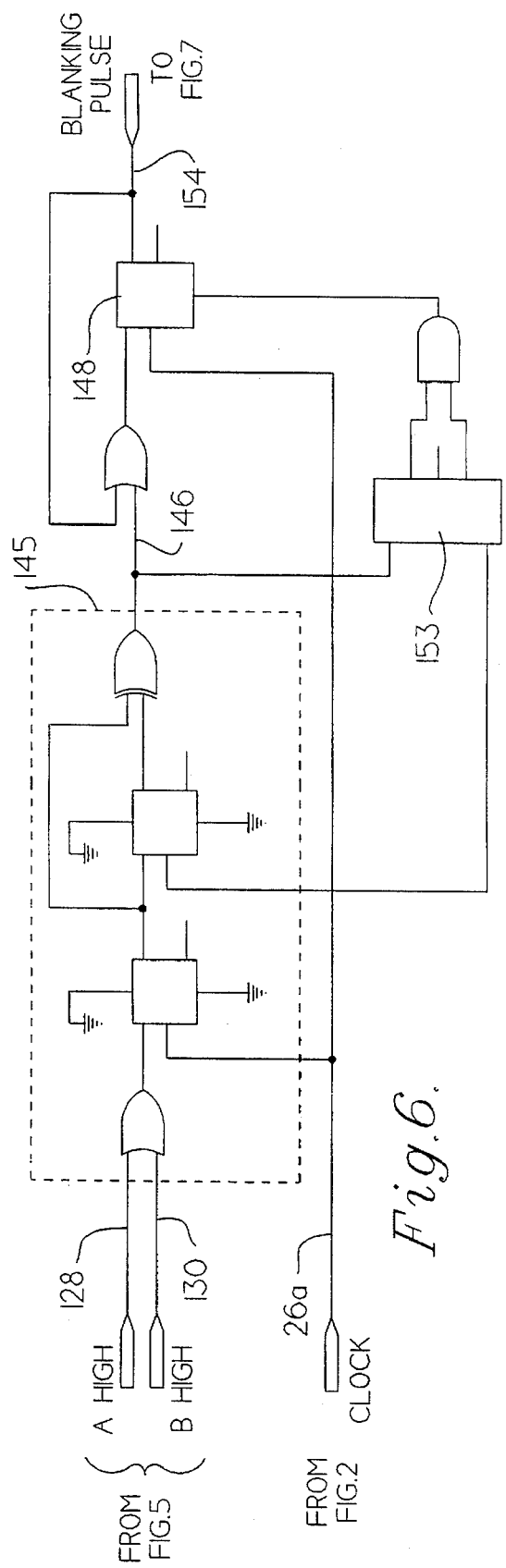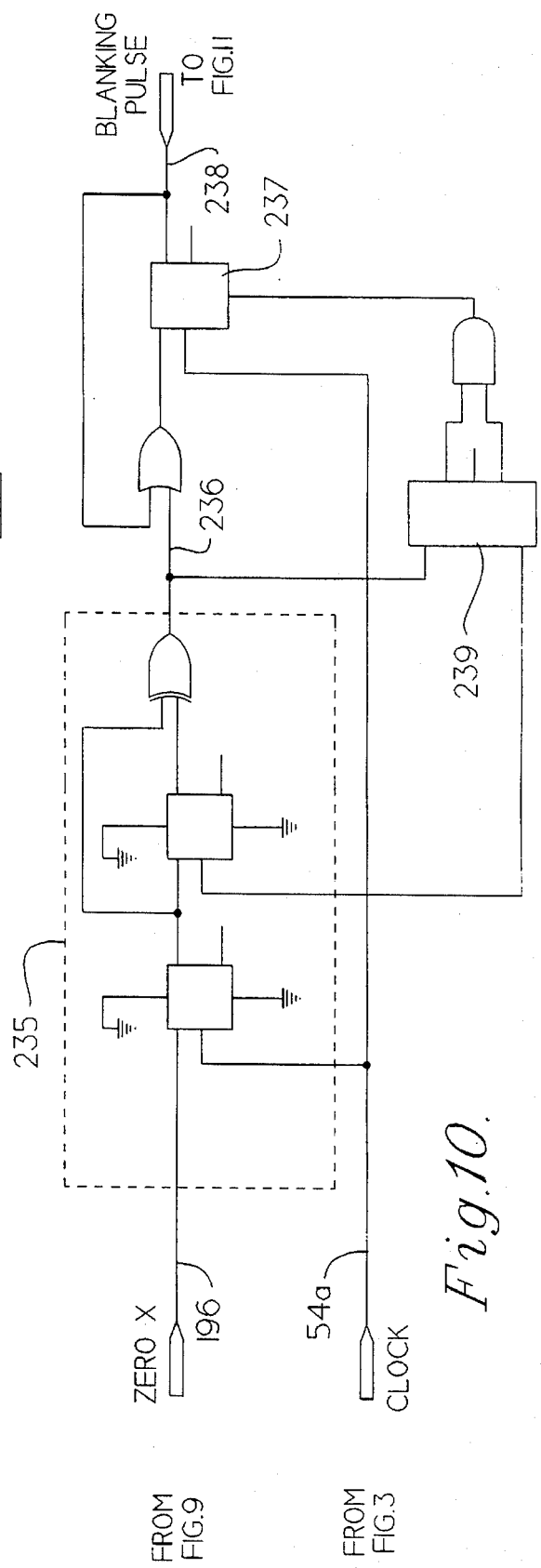

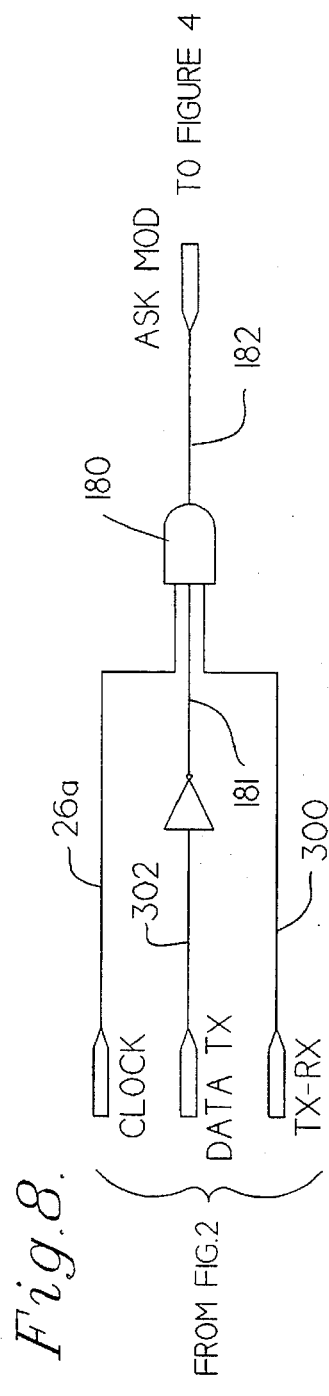
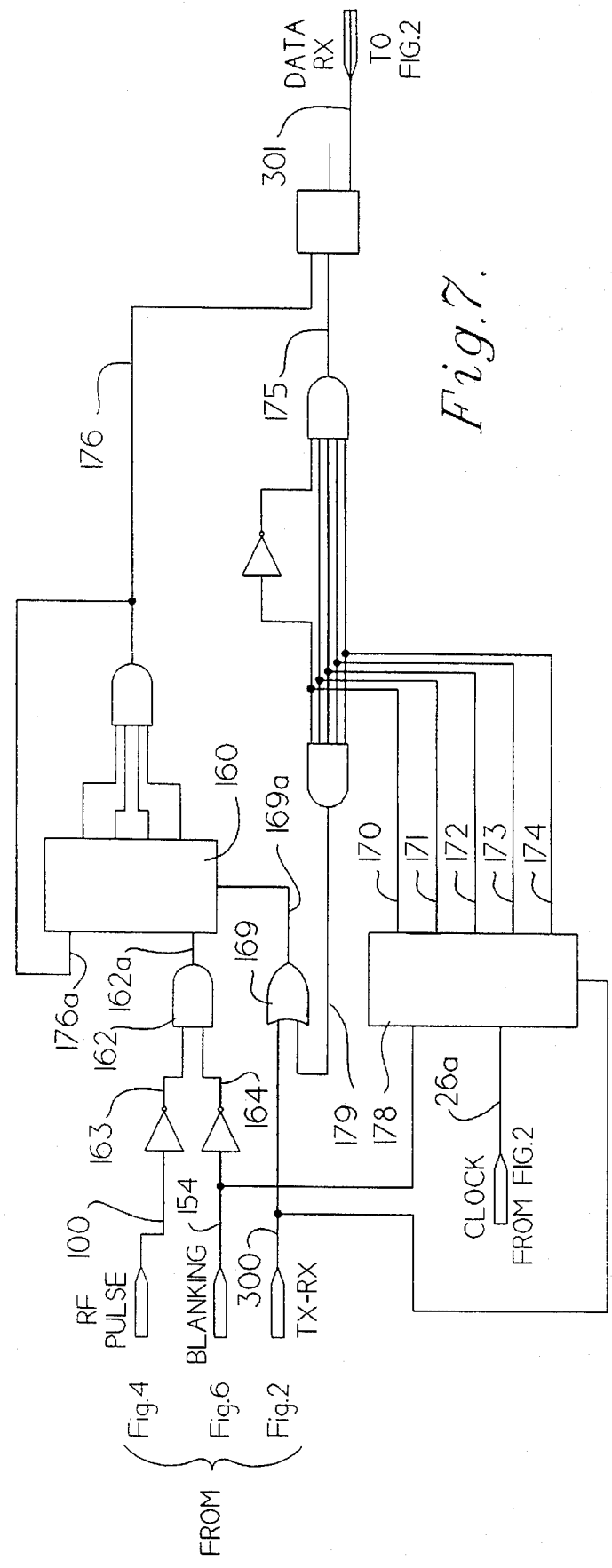
Fig. 7.
Fig. 8.

TRANSCUTANEOUS ENERGY AND INFORMATION TRANSMISSION APPARATUS

BACKGROUND OF THE INVENTION

1. Field of the Invention

The present invention relates to transcutaneous energy transmission systems wherein power and data is transmitted to implanted cardiac assist devices using an external transmitting coil and subcutaneously located receiving coil.

2. Description of the Art

The advent of implantable cardiac assist devices such as artificial hearts, ventricular assist devices, and the like, has lead to a concomitant need for a power source that meets the significant power requirements for such devices yet permits meaningful patient mobility.

One such power transmission system transcutaneously transmits power to a Left Ventricle Assist Device (LVAD), but has no provision for data communications. Given the complexity of many cardiac assist devices, there is a need to receive data from the device which may include ECG, blood pressure, and device status information, as well as transmit programming and control information to the device, as needed to maintain system operation. It is desirable to combine energy transmission and data communication into a unitary system.

Another power transmission system allows bidirectional data transmission at 300 to 1200 baud. However, this system limits the data transfer speeds by making the data link and power conversion circuitry interdependent. A data transmission rate of 1200 baud is not fast enough to allow continuous, high resolution monitoring of multiple signals such as ECGs, blood pressure, motor control waveforms, etc., used in advanced, implanted cardiac assist systems.

The present invention uses an external coupler in conjunction with subcutaneously-located coupler for both power and data transmission. The data transmission technique employed in the present invention can be capable of data transmission rates exceeding 19200 bits per second without compromising the power transmission scheme. The proposed transcutaneous energy and data transmission system provides data transmission speeds required for programming and monitoring advanced implanted cardiac assist systems.

SUMMARY OF THE INVENTION

An apparatus is provided for transcutaneously transmitting a first power signal to, and communicating first and second information signals with, an implantable device. The apparatus can include an external unit having first power means for generating the first power signal; first signalling means for generating the first information signal; first receiving means for receiving the second information signal; and first coupling means connected to the first power means, the first signalling means, and the first receiving means, for independently coupling the first power signal and said first information signal. The apparatus can also include an internal unit having second power means for receiving the first power signal; second signalling means for generating the second information signal; second receiving means for receiving the first information signal; and second coupling means connected to the second power means, the second signalling means, and the second receiving means, for independently coupling the first power signal and the second information signal.

The first power means transmits the power signal at a power frequency, and the first signalling means can transmit the first information signal at a frequency greater than the power frequency. The first power means may also include a power supply. The second signalling means, too, may transmit the second information signal at a frequency greater than the power frequency. However, the transmitting frequencies of the first and second information signals are not required to be the same and, indeed, may be different to provide, for example, fullduplex communication.

The external unit can include a power converter for converting a power input signal at a first preselected frequency to a first power signal at a power frequency; an external coupler coupled to the common transmission channel for transmitting the first power signal, and for communicating the first and second information signals; an external signal conditioner interposed between the external coupler and the power converter for symmetrically transceiving the first and second information signals; and an external data controller connected to the external signal conditioner for symmetrically controlling the first and second information signals.

The internal unit can include an internal coupler coupled to the common transmission channel for receiving the first power signal and for communicating the first and second information signals; a voltage regulator connected between the internal coupler and the implantable device, for converting the first power signal into a second power signal which is provided to the implantable device; an internal signal conditioner interposed between the internal coupler and the voltage regulator for symmetrically transceiving the first and second information signals; and an internal data controller connected between the internal signal conditioner and the implantable device, symmetrically controlling the first and second information signals. Symmetrically controlling includes amplitude-shift-keying modulation of a data signal upon a radio-frequency carrier signal of a preselected carrier frequency, which is presently preferred to be about 8 megahertz (MHz).

The external and internal couplers each can include a primary and secondary tuned circuit, respectively. Each tuned circuit has a resonant frequency which can be, for example, about 160 kilohertz (kHz). In addition, the first and second signal conditioners can include a first and second frequency-selective filter, respectively. Each frequency-selective filter can have respective upper and lower cutoff frequencies of about 7.9 MHz and about 8.1 MHz, with a central frequency of about 8 MHz.

External and internal data controllers can have first and second suppression means, respectively, for suppressing deterministic noise in the first and second information signals. Also, the voltage regulator can include shunting means for confining the power signal to the internal coupler when the signal current is about zero amperes. The shunting means can be synchronized to coincide with zero-crossings of the current, so that switching losses and electromagnetic interference are minimized thereby.

BRIEF DESCRIPTION OF THE DRAWINGS

FIG. 5 is a detailed block diagram of the H-bridge controller.

FIG. 6 is a simplified schematic of the external blanking pulse generator.

FIG. 7 is a simplified schematic of the external ASK demodulator.

FIG. 8 is a schematic of the external ASK modulator.

FIG. 10 is a simplified schematic diagram of the internal blanking pulse generator.

DETAILED DESCRIPTION OF THE PREFERRED EMBODIMENTS

Figure 1:
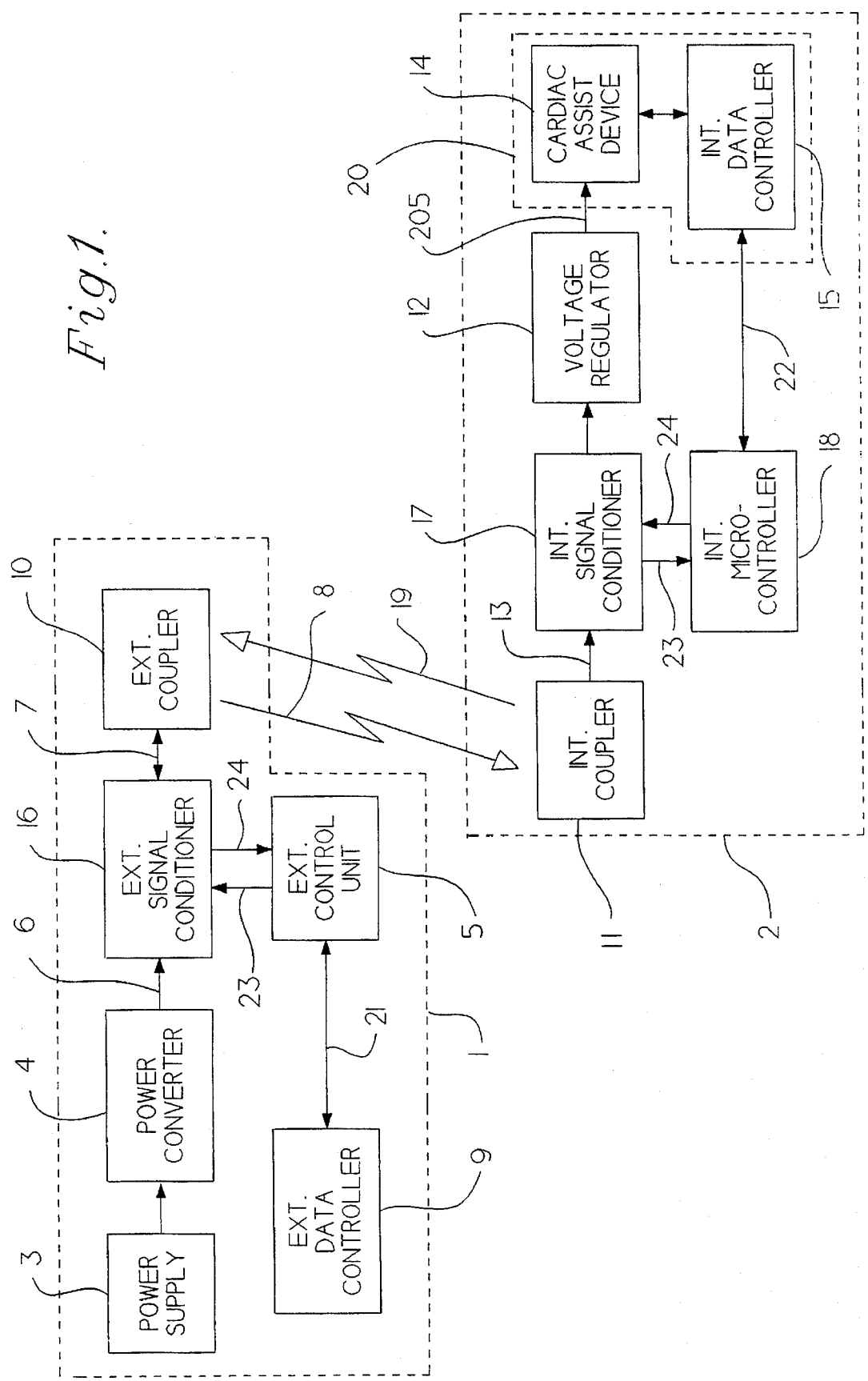
FIG. 1 is a general block diagram of the present invention.

FIG. 1 is a block diagram of the internal and external components of a transcutaneous energy and data transmission apparatus according to one embodiment of the present invention. In general, the apparatus can include external unit 1 which can be located external to the body, and internal unit 2 which can be implanted, for example, within the body of a patient.

The first power means of external unit 1 can include power converter 4. The first power means can also include power supply 3. External unit 1 can have a first signalling means for generating a first information signal 23 which can include external signal conditioner 16, in addition to particular components of external data controller 5 such as, for example, ASK modulator 39 and line driver 40, both in FIG. 2. The first signalling means may also include external control unit 9. The first receiving means can receive the second information signal 24 and can include external signal conditioner 16, and components of data controller 5 such as, for example, RF detector 37 and ASK demodulator 38, both in FIG. 2. The first receiving means may also include external control unit 9. Also, external unit 1 may include first coupling means for independently coupling the power signal and the first information signal 23. Such coupling means can be external coupler 10 which can have therewithin primary tuned circuit 31 in FIG. 2.

The second power means of internal unit 2 can include internal voltage regulator 12 which receives the power signal transmitted by external unit 1. Internal unit 2 can also include a second signalling means for generating the second information signal 24, which signalling means can include internal signal conditioner 17 and components of internal data controller 18 such as, for example, ASK modulator 59 and line driver 60, both in FIG. 3. The second signalling means may also include implantable device 20. The second receiving means can receive the first information signal 23 and can include internal signal conditioner 17, and components of data controller 18 such as, for example, RF detector 58 and ASK demodulator 57, both in FIG. 3. The second receiving means may also include implantable device 20. Also, internal unit 2 may include second coupling means for independently coupling the power signal and the second information signal 24. Such coupling means can be internal coupler 11 which can have therewithin secondary tuned circuit 46 in FIG. 3.

In external unit 1, power supply 3 may be a patient-worn DC battery belt or a stationary power supply physically separate from the patient. The DC battery belt can provide sufficient power at a suitable DC voltage, such as 12 VDC. The stationary power supply could secure input power from commercial 50/60 Hz AC power sources, and convert the AC input voltage to a suitable DC voltage, for example, 12 VDC, which is similar to the voltage produced by the battery belt.

Power converter 4 can convert electrical current from power supply 3 into a power frequency, i.e., high-frequency AC, current first power signal 6. A first information signal 23 can be received from external control unit 9 by external data controller 5 via external link 21. The preselected data in first information signal 23 may be, in turn, modulated onto a radio-frequency (RF) carrier signal by a suitable modulation technique such as, for example, amplitude-shift-keying (ASK) modulation within controller 5. It is preferred that the frequency of the RF carrier signal be greater than the power frequency, or frequency of the power signal. In one embodiment of the present invention, a single carrier frequency is used for transmission between units 1 and 2. It is preferred that the carrier frequency be about 8 MHz, although other frequencies may be equally suitable. However, different frequencies may be used for transmission by each of external unit 1 and internal unit 2, if such is desired, for example, to provide full-duplex information signal communication.

The data-modulated RF carrier signal can be received from controller 5 by external signal conditioner 16 and be mixed with power signal 6 by external signal conditioner 16, becoming outgoing composite external signal 7. Signal conditioner 16 can symmetrically transceive an information signal. That is, signal conditioner can act both to generate a data-modulated RF carrier signal bearing first information signal 23 for transmission to internal unit 2 and to receive a data-modulated RF carrier signal bearing second information signal 24 which may be received from internal unit 2. Such symmetric transceiving can be independent of power signal transmission by external unit 1.

Signal 7 can be provided to external coupler 10, which may have a tuned circuit with an induction coil therein, and can create in external coupler 10 a first magnetic field 8 responsive to signal 7. Magnetic field 8 thus can be representative of first power signal 6 or first information signal 23 bearing the data-modulated carrier signal, or both. Field 8 can be transmitted symmetrically between external unit 1 and internal unit 2 within the common transmission channel. The common transmission channel can traverse a composite of transmission media which can include non-ferrite cutaneous and pericutaneous entities such as air, clothing, tissue, body fluids, and the like.

Within internal unit 2, magnetic field 8 can induce an incoming composite internal signal 13 within internal coupler 11. Signal 13 can be representative of signal 7 because external coupler 10 and internal coupler 11 can act together as an air-core transformer. Signal 13 can include a data-modulated RF carrier signal imposed upon a high-frequency AC current. Voltage regulator 12 converts the first power signal, or high-frequency AC current of signal 13, into a second power signal such as, for example, regulated Vcc voltage signal 205, which may be used to energize implantable device 20. Implantable device 20 can include cardiac assist device 14, and internal microcontroller unit 15.

In addition, data which may still be in the form of a data-modulated RF carrier signal can be extracted from signal 13 by internal signal conditioner 17. Similar to external signal conditioner 16, internal signal conditioner 17 can symmetrically transceive first and second information signals. That is, signal conditioner 17 can act both to generate the second information signal 24 in the data-modulated RF carrier signal for transmission to external unit 1 and to receive first information signal 23 in the data-modulated RF carrier signal which may be received from external unit 1. Such symmetric transceiving can be independent of power signal transmission by external unit 1.

This data-modulated RF carrier signal can be demodulated within internal data controller 18 which in turn transmits the demodulated data stream to internal microcontroller 15 via internal link 22. Internal microcontroller 15 can transmit the received data to cardiac assist device 14.

Data can be transferred symmetrically between internal unit 2 and external unit 1. That is, a first or second information signal may be transmitted or received by device 20, respectively. For example, device 14 may provide data to internal microcontroller 15 which, in turn, transmits as data to internal data controller 18 via internal link 22. Internal microcontroller 15 itself may provide additional data to internal data controller 18 via internal link 22. Data controller 18 can modulate the outgoing data by any suitable scheme such as, for example, ASK modulation. Indeed, it is preferred that internal data controller 18 modulate outgoing data in the same manner as external data controller 5.

Similar to external data controller 5, data are ASK-modulated onto an RF carrier signal with a frequency of, for example, 8 MHz, by internal data controller 18. The data-modulated carrier signal can be provided to internal signal conditioner 17 which, in turn, can be input to internal coupler 11 in which a second magnetic field 19 representative of the outgoing data can be generated. Second magnetic field 19 impinges upon external coupler 10 thus inducing an electrical current therewithin, which current can be representative of the ASK-modulated carrier transmitted from internal unit 2. Signal conditioner 16 can direct the ASK-modulated carrier signal to external data controller 5 for demodulation such that the demodulated data stream can be provided to external control unit 9. External control unit 9 can be used to provide programming, control, diagnostic, and data collection functions in conjunction with implantable device 20.

Figure 2:
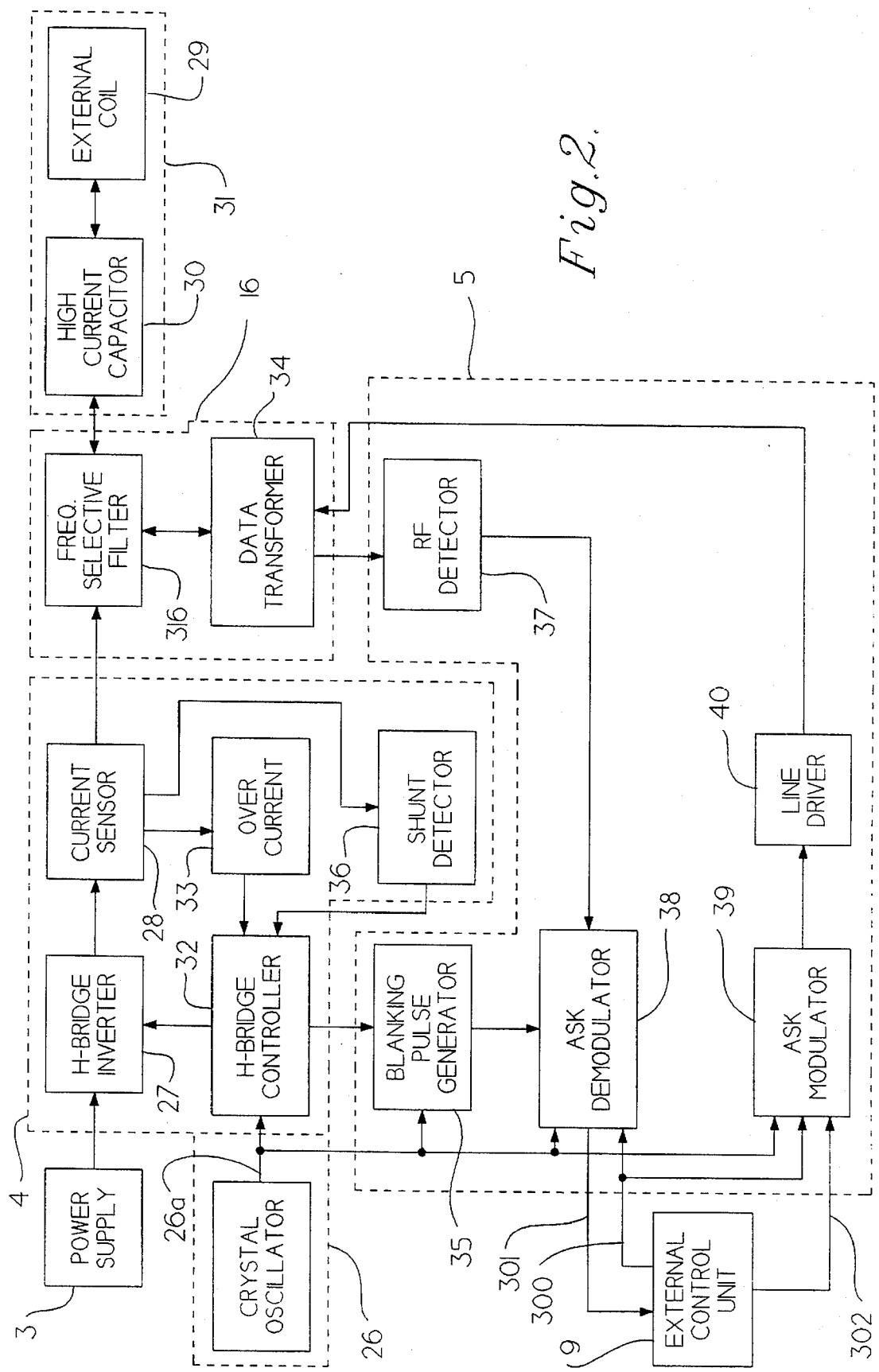
FIG. 2 is a detailed block diagram of the external electronics.

FIG. 2 further illustrates a present embodiment of external unit 1 as found in FIG. 1. As in FIG. 1, power supply 3 can provide DC power to power converter 4. In power converter 4, H-bridge inverter 27 can convert the voltage supplied by DC power supply 3 to an alternating voltage of a preselected frequency, which is the power frequency. The frequency of the alternating voltage is chosen to be substantially at the resonant frequency of primary tuned circuit 31 which may be within external coupler 10 in FIG. 1. Primary tuned circuit 31 may be composed of primary high-current capacitor 30 and primary external coil 29.

Primary tuned circuit 31 presents a low impedance path to the alternating voltage oscillating at the fundamental frequency of circuit 31, while substantially attenuating other harmonic frequencies. The resulting current through primary tuned circuit 31 is substantially sinusoidal when excited by a voltage source at preselected resonant frequency of primary tuned circuit 31. The preselected resonant frequency is chosen to provide a desired minimum power transmission level, such as 70 watts, to the internal components while using the lowest anticipated voltage from power supply 3 such as, for instance, 10 volts. In the present embodiment, the preselected resonant, or power, frequency is between about 152 kHz and 168 kHz, preferably between about 158.4 kHz and 161.8 kHz, and more preferably about 160 kHz.

In power converter 4, H-bridge controller 32 can determine both the duty cycle and the switching frequency of H-bridge inverter 27. In order to protect the components of external unit 1 from excessive currents, and to maintain efficient energy transfer to the components of internal unit 2, H-bridge controller 32 can utilize the inputs from over-current detector 33 and shunt detector 36. If the magnitude of the sinusoidal current through current sensor 28 exceeds a preselected maximum threshold, over-current detector 33 can signal H-bridge controller 32 to cease power transmission for one cycle.

Figure 3:
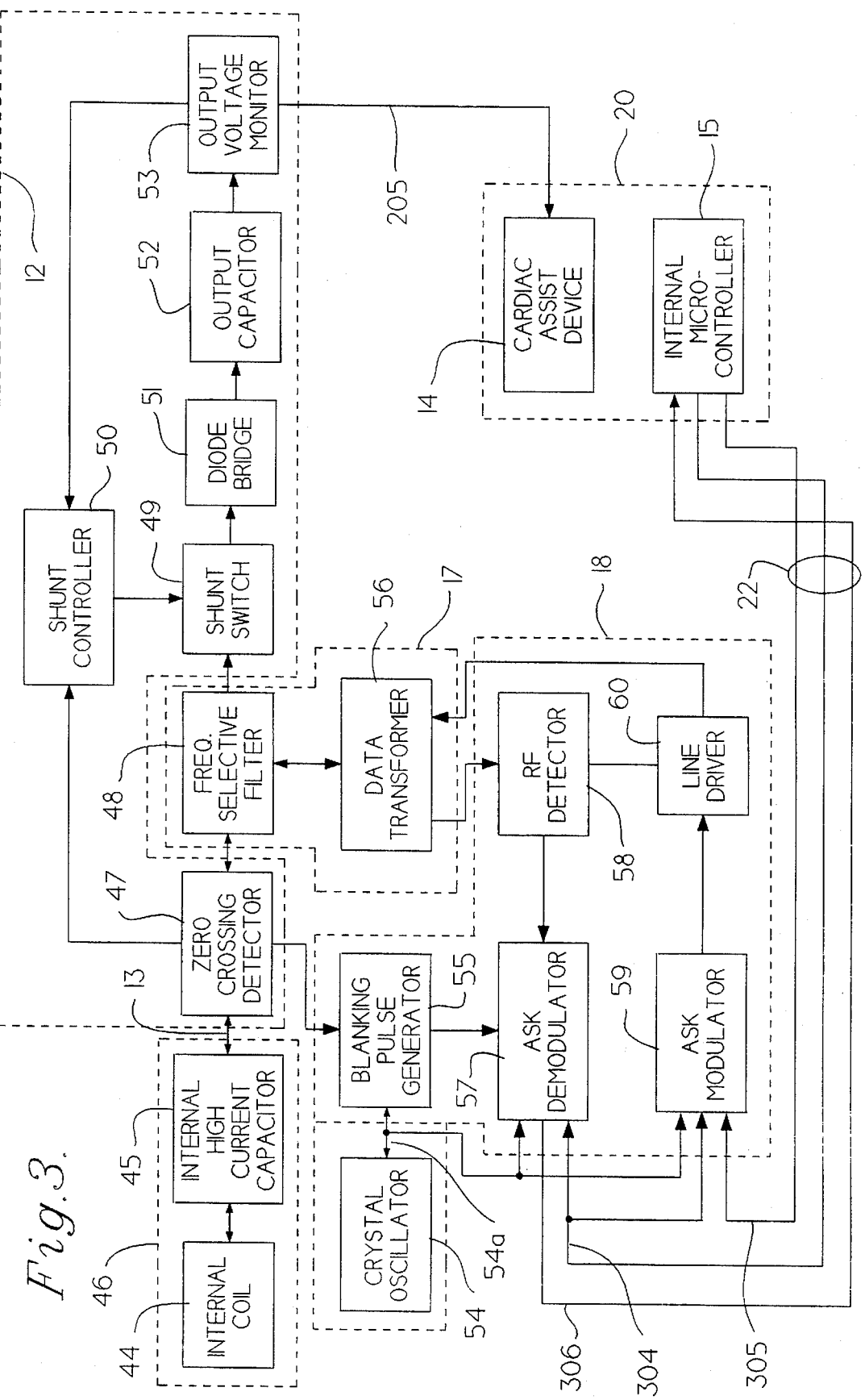
FIG. 3 is a detailed block diagram of the implanted electronics.

Shunt detector 36 monitors the voltage created by current sensor 28 to determine if there is a shunt across internal tuned circuit 46 (FIG. 3). If shunt detector 36 indicates that internal tuned circuit 46 (FIG. 3) is shunted, H-bridge controller 32 can reduce the duty cycle of H-bridge inverter 27 from nearly 100 percent to some lower value such as about 10 percent. Conversely, if internal tuned circuit 46 (FIG. 3) is not shunted, H-bridge inverter 27 can be driven at nearly 100 percent duty cycle. To maintain an accurate drive frequency to H-bridge inverter 27, H-bridge controller 32 uses a clock frequency derived from a clock circuit which may be crystal oscillator 26.

External link 21 between external control unit 9 and external data controller 5 in FIG. 1 can include three control lines, namely, tx_rx signal 300, data_rx signal 301, and data_tx signal 302, as seen in FIG. 2. Signal 300 signifies the transmit/receive control signal. Signal 301 signifies the data-to-be-received signal. Signal 302 signifies the data-to-be-transmitted signal. Each of signals 300, 301, and 302 can assume a value of either logic zero or logic one.

In one embodiment according to the present invention, when signal 300 is a logic one, ASK modulator 39 modulates the carrier frequency from crystal oscillator 26 with signal 302. Accordingly, when signal 302 is a logic one, ASK modulator 39 sends a logic zero to line driver 40. If signal 302 is a logic zero while signal 300 is a logic one, ASK modulator 39 permits clock signal 26a of crystal oscillator 26 to drive line driver 40 directly.

The differential output of line driver 40 can be coupled to external signal conditioner 16, which may have first frequency-selective filter 316 therewithin, the center frequency of the frequency-selective filter is preferred to be about the same as the carrier frequency used for modulation, here, about 8 Mhz. In an embodiment according to the invention herein, it is preferred that the respective lower and upper cutoff frequencies of filter 316 be about 7.84 MHz and 8.16 MHz, and preferably about 7.9 MHz and 8.1 MHz, with the center frequency being about 8 MHz.

Because first frequency-selective filter 316 in signal conditioner 16 can have a high impedance at frequencies near its central frequency, and low impedance otherwise, signal conditioner 16 can remain transparent to the power transmission circuitry, at power transmission frequencies, e.g., about 160 kilohertz. Thus, the power transmission current can pass, substantially unimpeded, serially through filter 316, while the approximately 8 MHz carrier frequency data signal causes a detectable voltage to be developed across filter 316.

In effect, filter 316 acts as a notch filter relative to the power transmission current, wherein all current frequencies except about 8 MHz are passed, and, conversely, as a bandpass filter relative to the data carrier voltage, wherein a voltage develops across filter 316 only in response to signals with frequencies around 8 MHz.

During data transmission, external signal conditioner 16 converts the square wave output of line driver 40 into a sinusoidal voltage for transmission through a transmission medium. The resulting voltage across signal conditioner 16 causes a high frequency current to flow in external coil 29. This magnetic field can be coupled to an internal coupler such as, for example, internal coupler 11 in FIG. 1.

During the demodulation process, i.e., when signal 300 is a logic zero, radio frequency current which can be induced in external coil 29, travels through first frequency-selective filter 316 in signal conditioner 16. Data transformer 34 senses and scales the voltage across first frequency-selective filter 316 and, thus, signal conditioner 16 and routes it to RF detector 37. RF detector 37 converts analog inputs above a preselected threshold to digital level pulses. With a logic zero on signal 300, ASK demodulator 38 receives the digital level pulses and extracts signal 301 therefrom.

The fast rise times employed by the transistors in H bridge inverter 27 can create bursts of broadband energy that may be coupled to signal conditioner 16. The resulting transient sine waves in signal conditioner 16 generate deterministic noise which could be misinterpreted as a valid RF signal. Therefore, a first suppression means for suppressing this, and other, deterministic noise can be employed, and may be specifically embodied by blanking pulse generator 35. Generator 35 can be used during data demodulation to create a blanking pulse of sufficient width, such as 750 nsecs to inhibit ASK demodulator 38 coincidentally with the critical edges of the input to H-bridge inverter 27.

FIG. 3 describes one embodiment of internal unit 2. Internal coupler 11 can include secondary tuned circuit 46 which itself may include internal coil 44 and internal high-current capacitor 45. Current circulating in primary tuned circuit 31 in FIG. 2 can induce an alternating current in secondary tuned circuit 46. This alternating current can be incoming composite internal signal 13 which may include high-frequency AC current power signal and a data modulated RF carrier signal. Signal 13 can be provided to internal signal conditioner 17, described below, for extraction of existing data and then provided to voltage regulator 12, also described below for conversion of the first power signal into the second power signal. The second power signal, which can be conditioned Vcc voltage signal 205, can be then provided to implantable device 20 to provide power for cardiac assist device 14.

In voltage regulator 12, Vcc voltage signal 205 can be maintained at a substantially constant amplitude by regulating the amount of current delivered to output capacitor 52. Diode bridge 51 and output capacitor 52 convert the alternating current to a direct current. When voltage signal 205 is approximately at a maximum, current can be directed away from output capacitor 52 and confined to internal tuned circuit 46 by shunting means which can be part of voltage regulator 12, and can include shunt controller 50 and shunt switch 49.

Shunting means can be responsive to zero-crossings of signal 13. Output voltage monitor 53 alerts shunt controller 50 whenever voltage signal 205 is at a preselected maximum voltage. When voltage signal 205 reaches the preselected maximum, such as, for example, 17 volts, shunt controller 50 can activate shunt switch 49 immediately after zero-crossing detector 47 indicates the sinusoidal current in internal tuned circuit 46 is zero. By turning on shunt switch 49 while it has near-zero current passing therethrough, i.e., by synchronizing the operation of shunt controller 50 and shunt switch 49 with zero-crossings of signal 13, shunting means can minimize switching losses, and electromagnetic interference. After voltage signal 205 drops to a preselected minimum value, for example, 16 volts, shunt controller 50 can turn off shunt switch 49 and allow current to flow through diode bridge 51 and then into output capacitor 52.

During data transmission from internal unit 2 to external unit 1, internal data controller 18 can receive information from internal microcontroller 15 through internal link 22, as seen in FIG. 1. As seen in FIG. 3, internal link 22 between internal microcontroller 15 and internal data controller 18 can include three control lines, namely, sec_tx_rx signal 304, sec_data_tx signal 305, and sec_data_rx signal 306. Signal 304 represents the secondary transmit/receive control signal. Signal 305 signifies the secondary data-to-be-transmitted signal. Signal 306 signifies the secondary data-to-be-received signal. Each of signals 304, 305, and 306 can assume a value of either logic zero or logic one.

When signal 304 is a logic one, ASK modulator 59 modulates the carrier frequency from crystal oscillator 54 with the data signal to be transmitted. Accordingly, when signal 305 is a logic one, ASK modulator 59 sends a logic zero to line driver 60. If signal 305 is a logic zero while signal 304 is a logic one, ASK modulator 59 allows crystal oscillator 54 to drive line driver 60 directly. The differential output of line driver 60 can be provided to internal signal conditioner 17 and can be coupled to second frequency-selective filter 48 through internal data transformer 56.

Similar to first frequency-selective filter 316 in FIG. 2, second frequency-selective filter 48 is preferred to have a central frequency about the carrier frequency of the modulated data, here, about 8 MHz. In an embodiment according to the invention herein, it is preferred that the respective upper and lower cutoff frequencies of filter 48 be about 7.84 MHz and 8.16 MHz, and preferably about 7.9 MHz and 8.1 MHz, with the center frequency being about 8 MHz.

Also similar to filter 316 in FIG. 2, second frequency-selective filter 48 can have a high impedance at frequencies near its central frequency, and low impedance otherwise. Therefore, signal conditioner 17 can remain transparent to the power transmission circuitry, at power transmission frequencies, e.g., about 160 kilohertz. The power transmission current can pass, substantially unimpeded, serially through filter 48, while the approximately 8 MHz carrier frequency data signal causes a detectable voltage to be developed across filter 48.

In an effect similar to filter 316 in FIG. 2, filter 48 in FIG. 3 acts as a notch filter relative to the power transmission current, wherein all current frequencies except about 8 MHz are passed, and, conversely, as a bandpass filter relative to the data carrier voltage, wherein a voltage develops across filter 48 only in response to signals with frequencies around 8 MHz.

During data transmission, second frequency-selective filter 48 converts the square wave output of line driver 60 to a sinusoidal voltage for transmission through the transmission medium. The resulting voltage across second frequency-selective filter 48 causes high frequency current to flow in internal coil 44, inducing a magnetic field which can be coupled to external coil 29 in external coupler 10 in FIGS. 1 and 2.

During the demodulation process, i.e., when data is being received from external unit 1, the RF current induced in internal coil 44 passes through second frequency-selective filter 48. Because filter 48 has a high impedance at its center frequency, for instance, 100 ohms, current flowing through second frequency-selective filter 48 creates a voltage thereacross. At power transmission frequencies, second frequency-selective filter 48 presents a very low impedance and thus remains transparent to the power reception circuitry. Data transformer 56 scales the voltage across second frequency-selective filter 48 and directs it to RF detector 58. RF detector 58 converts analog inputs above a preselected threshold value to digital level pulses. During demodulation, signal 304 is a logic zero causing ASK demodulator to receive the digital level pulses from RF detector 58, and extract the secondary data to be received, i.e., signal 306. Signal 306 can be designated sec_data_rx signal.

When current through secondary tuned circuit 46 crosses zero amplitude, the resultant bias reversal of diode bridge 51 can induce transients across second frequency-selective filter 48, which may be sinusoidal. Such transient waves in filter 48 are deterministic noise which could be misinterpreted as a valid RF signal. Therefore, a second suppression means for suppressing such deterministic noise can be employed, and may be specifically embodied by blanking pulse generator 55. Blanking pulse generator 55 can be synchronized to create a blanking pulse of sufficient width, such as, for example, 500 nsecs, to inhibit ASK demodulator 57 coincidentally with the zero current crossings of secondary tuned circuit 46. Zero-crossing detector 47 can trigger blanking pulse generator 55 to effect noise suppression.

Figure 4:
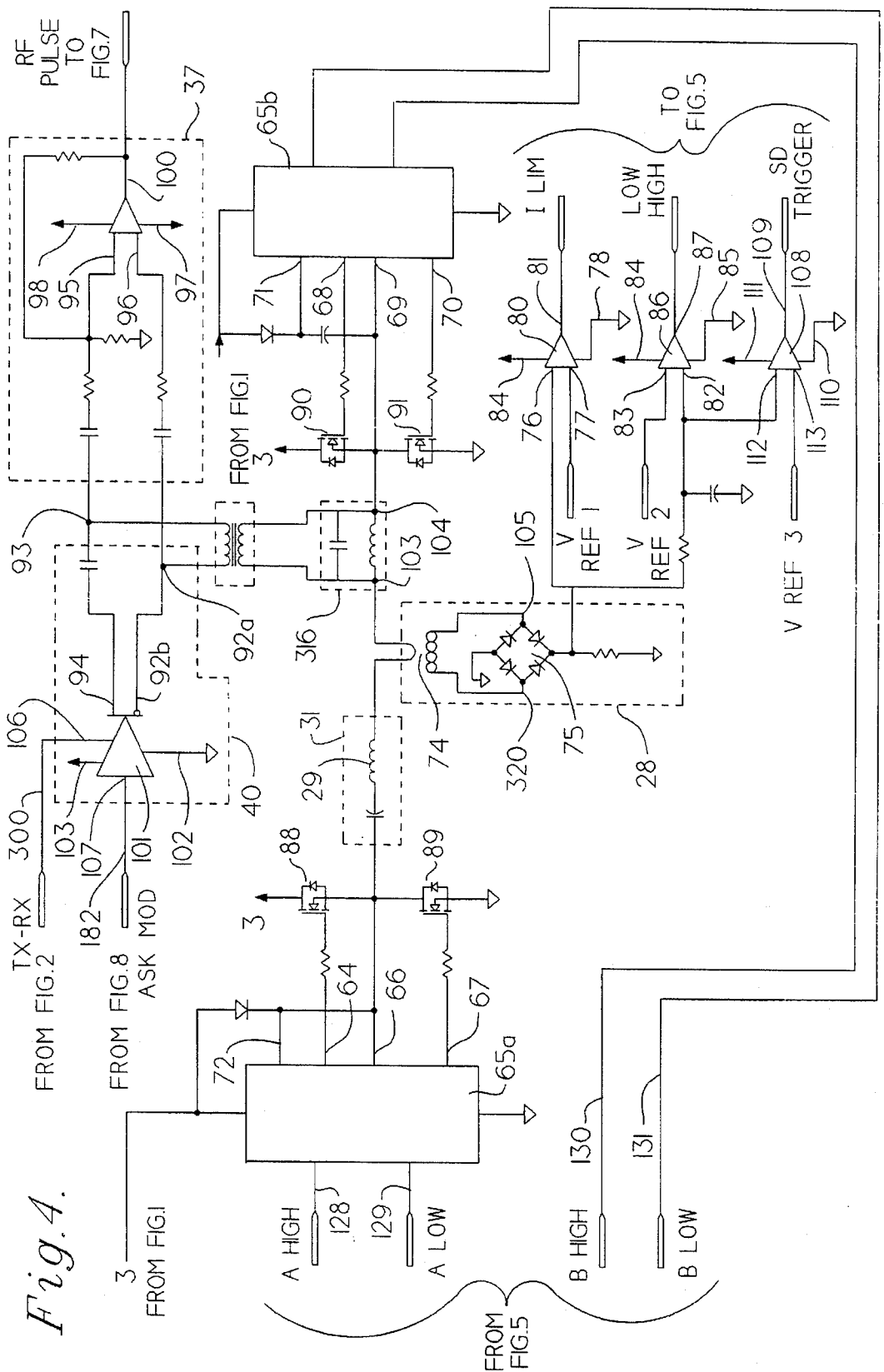
FIG. 4 is a schematic diagram of a portion of the external electronics.

FIG. 4 further illustrates an embodiment of external apparatus circuitry excluding the digital logic implemented within a programmable logic device (PLD). Control signals 128, 129, 130, and 131 (FIG. 5) control H-bridge driver 65a and 65b outputs 64, 67, 68, and 70. MOSFETs 88, 89, 90 and 91, along with primary tuned circuit 31, comprise an H-bridge. High current driver outputs 64, 67, 68, 70 drive the gate inputs of the MOSFETs in the H-bridge. Driver output 66, diode D2, and capacitor C5 create a level shifted supply voltage at driver lead 72 that can be approximately twice the voltage provided by power supply 3 (FIG. 1). The voltage at driver lead 72 can be used to create a drive voltage at output 64 sufficient to turn on N-channel MOSFETs. Likewise, driver pin 69, diode D3, and capacitor C6 create a bootstrapped supply for driver lead 71. Level shifting the output voltage of outputs 64 and 68 allows the H-bridge to contain all N-channel MOSFETs with low on resistance. This, in turn, maximizes power conversion efficiency.

Current sensor 28 senses a voltage representing the current flowing in primary tuned circuit 31. Current circulating through the H-bridge can be scaled by current transformer 74 and routed to diode bridge 75 through leads 320 and 105. The rectified current develops a ground-referenced voltage across R1, which can be connected to non-inverting input 76 of comparator 80. Comparator 80 has its inverting terminal 77 connected to a reference voltage source Vref1, positive supply terminal 70 connected to a five-volt source, negative supply terminal 78 connected to ground potential, and output to terminal 81.

As configured, output terminal 81 can be high whenever the current through primary tuned circuit 31 can be above a set threshold such as, for example, 25 amperes. Input 76 can be connected to inverting comparator input 82 of comparator 86 through a low pass filter formed by R7 and C4. Non-inverting terminal 83 can be connected to another voltage reference Vref2, which may be derived from Vref1 terminal 77. Comparator 86 includes a positive supply terminal 84 connected to a five-volt source, negative supply terminal 85 attached to ground potential, and a terminal for comparator output 87. Comparator output 87 can be asserted high when the average current through primary tuned circuit 31 is below a set threshold. Comparator input 82 can be also tied to non-inverting input 112 of comparator 108. Comparator 108 includes positive supply terminal 111 connected to a five-volt source, negative supply terminal 110 attached to ground potential, and comparator output terminal 109. Inverting input 113 can be connected to a voltage reference Vref3. Comparator output terminal 109 is asserted when the average current through primary tuned circuit 31 is above a set threshold such as, for example, 13 amps.

FIG. 4 illustrates the components that can be used for data transmission and reception. During data reception, high frequency current induced in external coil 29 creates a voltage across first frequency-selective filter leads 103 and 104, which are also connected to data transformer 34. Inductor L1 connected between leads 103 and 104 can be a small air core inductor ($\approx$40 nH) having a small inductance in comparison to the much larger external coil 29 ($\approx$1.9 uH). By making L1 a small air core inductor, resistance of the coil can be minimized ($\approx$4 milliohms) and thus has minimal effect on power transmission efficiency.

Lead 92a of transformer 34 can be connected to output lead 92b of line driver 101. Line driver 101 includes another output lead 94, which can be connected to transformer lead 93 through a decoupling capacitor C1. Lead 103 can be connected to a five-volt supply source while negative supply pin 102 can be connected to ground. Output pins of driver 101 are controlled by enable pin 106 and input pin 107. If enable pin 106 is held logic low, output leads 92b and 94 can be put in tri-state mode, and electrically disconnected from transformer leads 92a and 93. Alternately, leads 92b and 94 can be isolated from the transformer leads with active switches.

Input pin 107 is driven by ASK_mod on output 182. When line driver 101 is enabled by a logic one from tx_rx signal 300, differential output leads 94 and 92b drive data transformer 34 through transformer leads 93 and 92a. Data transformer 34 generates a scaled sinusoidal output voltage across leads 103 and 104 while isolating line driver 40 block from the high currents in first frequency-selective filter 316. The voltage across first frequency-selective filter terminals 103 and 104 is effectively in parallel with external coil 29 at frequencies well above the resonant frequency of primary tuned circuit 31. The high frequency voltage across external coil 29 can be then coupled to internal coil 44 in FIG. 3.

The data demodulation circuit contains a high-speed comparator 99 with output lead 100, positive supply pin 98, negative supply pin 97, non-inverting input 95, and inverting input 96. Supply pin 98 can be attached to a five-volt supply, while supply pin 97 can be connected to a minus five-volt supply. Inverting input 96 can be attached to 92a through a high pass filter. The high pass filter formed by C3, R3, and R4 reduces the effects of signals near the power transmission frequencies such as, for example, 160 kHz upon the operation of RF detector 37. R5 and R6 also prevent the voltages on input 96 from exceeding the common-mode range of comparator 99 while line driver 101 is enabled.

Non-inverting input 95 can be connected to transformer lead 93 through the high pass filter formed by C2, R2, and R5. Again, this filter reduces the effects of signals near the power transmission frequencies upon RF detector 37 and can ensure proper common-mode operation of comparator 99. Resistor R6, connected between lead 100 and input 95, provides positive hysteresis to non-inverting input 95. The value of R6 sets the minimum required amplitude of a signal between transformer leads 92a and 93 such that is considered a valid signal. As configured, lead 100 can remain high until the voltage differential between input 95 and input 96, such as 500 millivolts, is sufficient enough to cause lead 100 to pulse low.

FIG. 5 is a diagram representative of H-bridge controller 32, which is designed to control the switching sequence of the switches used in a standard H-bridge inverter configuration. Control signals 128, 129, 130, and 131 control the state of H-bridge drivers 65a and 65b (FIG. 4). Specifically, outputs A_high, control signal 128, and B_high, control signal 130 control the on-time, or duty cycle, of each leg of the H-bridge. Outputs A_high, control signal 128 and B_low, control signal 131, constitute one leg of the drive sequence while B_high, control signal 130, and A_low, control signal 129, make up the other leg. Drive_A 127 and Drive_B 126 units are arranged such that adequate dead-time, such as 250 nanoseconds (nsecs), can be provided between drive sequences. This dead-time allows H-bridge inverter 27 (FIG. 2) to change phase without creating any shoot-through currents. The dead-time can be controlled by dead_clock signal 138.

The timing sequences for H-bridge controller 32 are derived from crystal oscillator 26 (FIG. 2) output frequency. First, clock divider 124 divides crystal oscillator 26 output frequency, for example 8 MHz, to the output signals that include drvclk signal 132, dead-clock signal 138, and duty-clock signal 133. One cycle of drvclk signal 132 constitutes a power switching cycle in H-bridge controller 32. The pulse width of duty clock output signal 133 controls the duty cycle of H-bridge controller 32 while it is in low-duty-cycle mode.

The frequency of drvclk signal 132 can be at twice the preselected resonant frequency of primary tuned circuit 31 (FIG. 2). Toggle register 123 uses drvclk signal 132 input to create an output 137 that toggles the power switching phase of control signals 128, 129, 130 and 131.

Current limit control unit 120 use drvclk signal 132 and I_lim signal on output terminal 81 (FIG. 4) to create a signal on output 134. Output 134 can be routed to output decoder unit 125 and eventually turns off active control signals 128 or 130 until the next rising edge on drvclk signal 132.

Shutdown unit 121 has inputs of the sd_trigger signal on comparator output terminal 109 (FIG. 4) and drvclk signal 132. When the sd_trigger signal on terminal 109 is active (average current in primary tuned circuit out of range), output 135 can turn off control signals 128 and 130 indefinitely.

Duty cycle control unit 122 controls the duty cycle of the output registers. The duty cycle of a power cycle can be between about 10 percent to nearly 100 percent. If the low_high signal on comparator output 87, i.e, the shunt detector input (FIG. 4), is a logic one, output signal 136 can place the output registers in an approximately 10 percent duty cycle. Duty_clock signal 133 can control the duty cycle. Once comparator output 87 indicates internal tuned circuit 41 (FIG. 3) is no longer shunted, duty cycle control unit 122 can allow nearly 100 percent duty cycle power transmission to resume.

Decoder unit 125 takes outputs 134, 135, 136, and 137 and routes the appropriate logic levels to Drive_A unit 127 and Drive_B unit 126. Units 126 and 127 use outputs 139 and 140 to place control signals 128, 129, 130, and 131 in the appropriate state.

FIG. 6 represents one possible implementation of blanking pulse generator 35. When an upper MOSFET in the H-bridge is switched on or off, first frequency-selective filter 316 in FIG. 2 oscillates, or rings out, as result of the broadband energy created by switching the MOSFET, thus constituting another source of deterministic noise. Because edges on either A_high, i.e., control signal 128, or B_high, i.e., control signal 130, initiate the switching of an upper MOSFET in the H-bridge, they are used to initiate the blanking pulse. When edge detector 145 detects edges on either control signals 128 or 130, output 146 toggles to a logic one state for one cycle of timing circuit 26, for example, 125 nsecs. A logic one on output 146 causes blank register 148 to place a logic one on blanking pulse 154. A logic one at 146 also triggers one-shot counter 153 to begin counting. After one-shot counter 153 reaches the desired count, such as decimal 7, blank register 148 can be reset and blanking pulse 154 can return to a logic zero until the next edge is detected at control signals 128 or 130. The width of blanking pulse 154, for example 750 nsecs, can be chosen to ensure that the ringing in first frequency-selective filter 316 (FIG. 2) can not be interpreted as a valid signal.

FIG. 7 is a schematic circuit diagram of the ASK demodulator used in the apparatus. A logic zero on blanking pulse 154 and a falling edge of RF_pulse input on lead 100 enables AND gate 162 to supply counter 160 with a rising clock edge. RF_pulse input on lead 100 can be the output of comparator 144 from FIG. 4. When blanking pulse 154 from FIG. 6 is a logic one, sample_clk signal 162a can be held at a logic zero level. This prevents sample counter 160 from incrementing its count during an active blanking pulse 154. Any pulses on lead 100 can be ignored while blanking pulse 154 is a logic one. If counter outputs 165, 166, 167, and 168 are all a logic one, i.e., decimal count 16, input 176a can hold counter 160 in that state until a logic one on output 169a resets counter 160 back to zero. When tx_rx signal 300 is a logic one, i.e., transmit mode, OR gate 169 is enabled, and counter 160 can be cleared by output 169a.

Five-bit-period counter 178 increments its output with each clock pulse on clock signal 26a while tx_rx signal 300 is a logic zero. A logic one on blanking pulse 154 can hold period counter 178 in its current state. When period counter outputs 171, 172, 173, and 174, are a logic one and output 170 is a logic zero, clock signal 175 can clock demod register input 176. Input 176 is a logic one only if RF pulse counter 160 is at decimal count 16. By way of example, if 16 or more RF pulses on lead 100 are detected by RF pulse counter 160 in the time it takes period counter 178 to count 31 clock pulses on signal 26a, data_rx signal 301 will be a logic zero. Otherwise, it will be a logic one. On the 32nd clock pulse input 26a, period counter 178 outputs 170, 171, 172, 173, and 174 will all be a logic one and output 179 can enable OR gate 169 and reset RF pulse counter 160 to zero. On the next rising edge of signal 26a, period counter outputs 170, 171, 172, 173, and 174 can reset to a logic zero, and a new sampling period will begin. During transmit mode, while tx_rx signal 300 is a logic one, period counter 178 outputs 170, 171, 172, 173, and 174 can be reset to logic zero.

ASK modulator 39 in FIG. 2 used in the apparatus is shown in the schematic representation in FIG. 8. Three-input AND gate 180 has inputs clock line 26a, data_tx signal 302, and tx_rx signal 300. A logic one on tx_rx signal 300 input activates ASK modulator 39. The data to be transmitted, data_tx signal 302, is inverted, and then applied to AND gate 180. Output 182 can be either clock signal 26a or a logic zero. In this configuration, an RF carrier can be transmitted when signal 301 is a logic zero.

Figure 9:
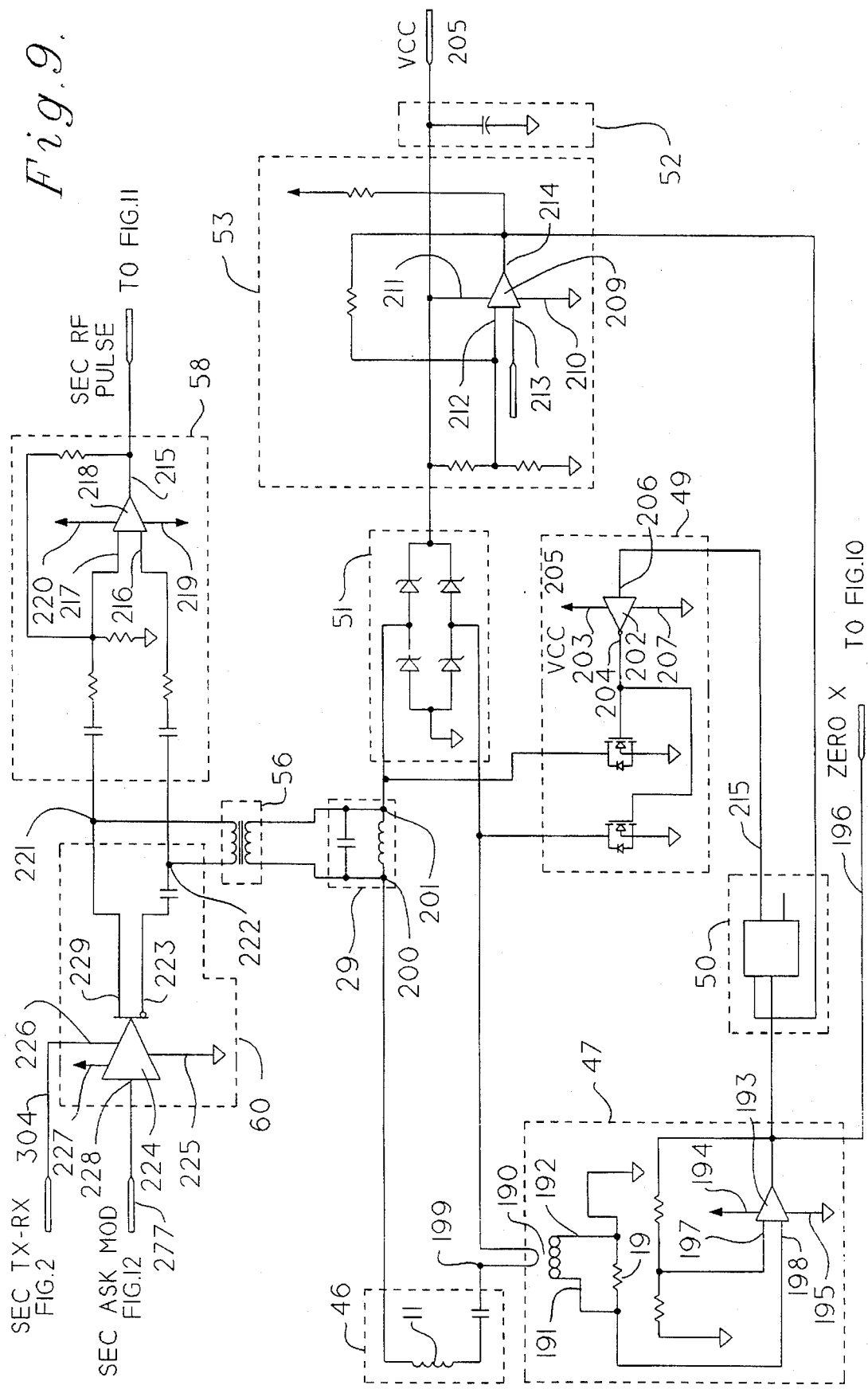
FIG. 9 is a schematic diagram of a portion of the internal electronics.

A portion of the internal apparatus electronics is shown in FIG. 9. Current circulating through internal tuned circuit 46 can be scaled by transformer 190 consisting of output terminals 191 and 192. Terminal 192 can be tied to ground potential. Terminal 191 can be connected to resistor R19 and inverting terminal 198 of comparator 193. Comparator 193 has its positive supply terminal 194 connected to a five-volt source and negative supply terminal 195 connected to a minus five-volt potential. Output terminal 196 can be connected to non-inverting input 197 through resistor R17. Non-inverting input 197 can be also connected to resistor R11. The resistor combination of R17 and R18 provide a small, for example 10 mV, positive hysteresis to non-inverting input 197. Output terminal 196 of zero-crossing detector 47 changes state each time the sinusoidal current through internal tuned circuit 46 crosses zero.

Shunt switch 49 can be connected across internal tuned circuit 46 at leads 201 and 199. Shunting MOSFET Q1 has its drain connected to lead 201, source connected to ground potential, and gate tied to output pin 204 of MOSFET driver 202. MOSFET Q2 has its drain connected to lead 199, its source connected to ground potential, and its gate tied to output pin 204 of MOSFET driver 202. The MOSFET driver has positive supply terminal 203 connected to Vcc voltage signal 205, negative supply terminal 207 connected to ground potential, input pin 206 connected to shunt signal 315, and inverted output pin 204 connected to the gate inputs of Q1 and Q2. When a logic low is received on input 206, Q1 and Q2 are turned on. With Q1 and Q2 on, leads 199 and 200 of internal tuned circuit 46 are shorted together through ground. This prevents current from flowing through diode bridge 51 and into output capacitors 52.

Voltage comparator 209, of output voltage monitor 53, has a positive supply terminal 211 connected to Vcc voltage signal 205, negative supply terminal 210 connected to ground potential, and output pin 214 connected to resistors R15 and R16. Inverting input 213 can be tied to a reference voltage Vref4. Non-inverting input 212 connected to hysteresis resistor R16 and the output of the voltage divider formed by R12 and R14. As voltage signal 205 rises, output pin 214 can remain at a logic low state until signal 205 reaches its maximum desired level such as 17 volts. When signal 205 reaches its maximum, pin 214 can switch to a logic one level and signal shunt controller 50 to activate shunt switch 49. Output pin 214 can remain at a logic one until the energy stored in output capacitors 52 is drained by the load and voltage signal 205 falls to its minimum value such as 16 volts. Once pin 214 falls to a logic zero, shunt controller 50 can deactivate shunt switch 49 at the next zero-current crossing edge on output terminal 196.

Also shown in FIG. 9 are the components used for data transmission and reception. During data reception, high frequency current induced in internal coil 44 creates a voltage across second frequency-selective filter leads 200 and 201, which are connected to data transformer 56 terminals. The inductor L1 connected between leads 200 and 201 can be a small air core inductor (≈60 nH) having a small inductance in comparison to the much larger internal coil 44 (≈15 uH). Also by making L1 a small air core inductor, resistance of the coil can be minimized and thus have little effect on power transmission efficiency. Data transformer lead 221 can be connected to output line 229 of line driver 224. Line driver 224 also includes output line 223 which can be connected to data transformer lead 222 through a decoupling capacitor C5. Power supply terminal 227 can be connected to a five-volt supply source while negative supply pin 225 can be connected to ground. The output of line driver 224 is controlled by enable pin 226 and input pin 228. If enable pin 226 is held logic low, output lines 229 and 223 can be put in tri-state mode and electrically disconnected from data transformer leads 221 and 222. Alternately, lines 229 and 223 can be isolated from the transformer leads with active switches. Input pin 228 can be driven by sec_data_tx signal 305.

When line driver 214 is enabled, differential output lines 229 and 223 drive transformer T1 through leads 221 and 222. Data transformer 56 generates a scaled sinusoidal output voltage across leads 200 and 201 while isolating line driver 60 block from the high currents in second frequency-selective filter 48. The voltage across frequency-selective filter terminal leads 200 and 201 is effectively in parallel with internal coil 44 at frequencies well above the resonant frequency of internal tuned circuit 46. The high frequency voltage across internal coil 44 can be then coupled to external coil 29.

RF detector 58 contains high speed comparator 218 with output pin 215, positive supply pin 220, negative supply pin 219, non-inverting input 217, and inverting input 216. Supply pin 220 can be attached to a five-volt supply, while supply pin 219 can be connected to a minus five-volt supply. Inverting input 216 can be attached to lead 222 through a high pass filter. The high pass filter formed by C6, R8, and R11 reduces the effects of signals near the power transmission frequencies, for example, 160 kHz, upon the operation of RF detector 58. R8 and R11 also prevent the voltages on input 216 from exceeding the common-mode range of amplifier 218 while line driver 60 is enabled.

Non-inverting input 217 can be connected to lead 221 through the high pass filter formed by C7, R9, and R10. Again, this filter reduces the influence of signals near the power transmission frequencies upon RF comparator 218 and substantially ensures proper common-mode operation of amplifier 218. Resistor R12, connected between output 215 and input 217, provides positive hysteresis to non-inverting input 217. The value of R12 sets the minimum required amplitude of a signal between leads 221 and 222 such that it can be considered a valid signal.

Referring to FIG. 3, when the current through internal tuned circuit 46 crosses through zero, the voltage across diode bridge 51 reverses. This bias reversal induces deterministic noise across second frequency-selective filter 48 which can be counteracted by second suppression means, as embodied, for example, by the blanking pulse generator shown in FIG. 10. Because edges on the zero_x signal on output terminal 196 represent zero-current crossings in internal tuned circuit 46 (FIG. 3), the zero_x signal on output terminal 196 can be used to initiate a blanking pulse for the purpose of data reception. When edge detector 235 in FIG. 10 detects an edge on output terminal 196, output 236 toggles to a logic one state for one cycle of crystal oscillator signal 54a, for example 125 nsecs.

A logic one on output 236 causes blank register 237 to place a logic one on its output 238. A logic one at output 236 triggers one-shot counter 239 to begin counting. After one-shot counter 239 reaches the desired count, such as, for example, decimal 5, blank register 237 can be reset and blanking pulse 238 can return to a logic zero until the next edge is detected at output terminal 196. The width of blanking pulse 238, for example 500 nsecs, can be chosen to ensure that the ringing in second frequency-selective filter 48 (FIG. 3) will not be interpreted as a valid signal.

Figure 11:
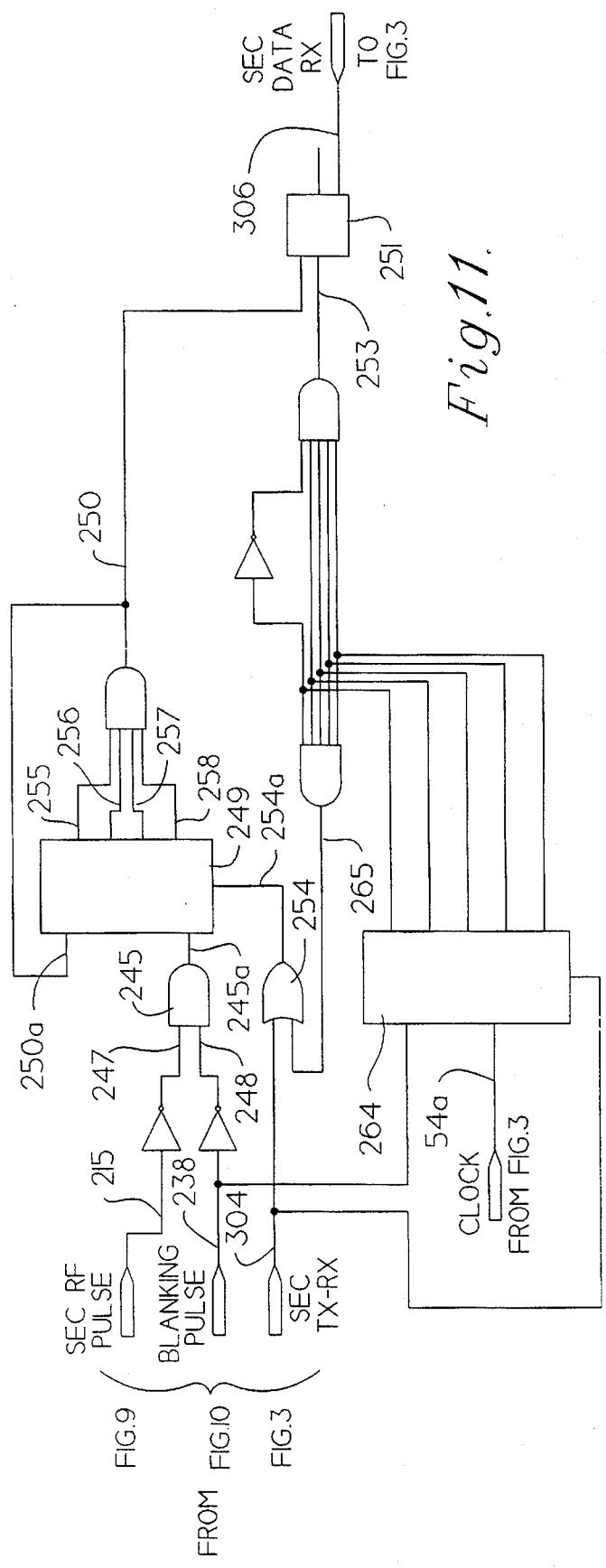
FIG. 11 is a simplified schematic diagram of the internal ASK demodulator.

FIG. 11 is a schematic circuit diagram of the ASK demodulator used in the apparatus. A logic zero on blanking pulse input 238 and a falling edge on the RF_pulse input on output pin 215 enables AND gate 245 to RF pulse counter 249 with a rising clock edge. The RF_pulse input on output pin 215 is the output of comparator 218 from FIG. 9. When blanking pulse input 238 from FIG. 10 is a logic one, output 245a can be held at a logic zero level. This prevents RF pulse counter 249 from incrementing its count during an active blanking pulse on 238. Any pulses on output pin 215 can be ignored while blanking pulse line 238 is a logic one.

If counter outputs 255, 256, 257, and 258 are all a logic one, i.e., decimal count 16, input 250a can hold RF pulse counter 249 in that state until a logic one on output 254a resets counter 249 back to zero. When sec_tx_rx line 304 is a logic one, i.e., transmit mode, OR gate 254 can be enabled, and counter 249 can be cleared by output 254a.

Five-bit-period counter 264 increments its output with each clock pulse on 54 while sec_tx_rx_signal 304 is a logic zero. A logic one on blanking line 238 can hold period counter 264 in its current state. When period counter outputs 260, 261, 262, and 263 are a logic one, and output 259 is a logic zero, clock signal 253 can clock demod register 251. Input 250 is a logic one only if RF pulse counter 249 is at decimal count 16. By way of example, if 16 or more RF pulses on output pin 215 are detected by RF pulse counter 249 in the time it takes period counter 264 to count 31 clock pulses on signal 54a, sec_data_rx output will be a logic zero. Otherwise, it will be a logic one. On the 32nd clock pulse signal 54a, period counter outputs 259, 260, 261, 262, and 263 will all be a logic one, and output 265 can enable OR gate 254, resetting RF pulse counter 249 to zero. On the next rising edge of signal 54a, period counter outputs 259, 260, 261, 262, and 263 can reset to a logic zero, and a new sampling period will begin. During transmit mode, while sec_tx_rx 304 is a logic one, period counter 264 outputs 259, 260, 261, 262, and 263 can be reset to logic zero.

Figure 12:
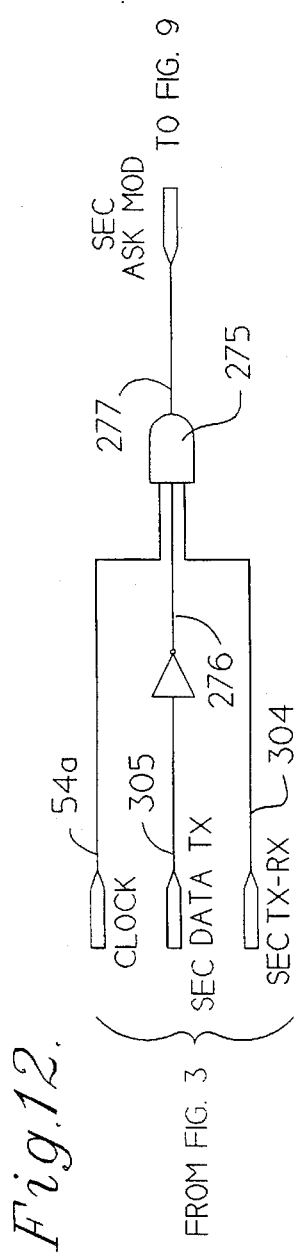
FIG. 12 is a schematic of the internal ASK modulator.

Internal ASK modulator 59 used with internal link 22 is shown in the schematic representation in FIG. 12. Three-input AND gate 275 has inputs clock 54, sec_data_tx 305, and sec_tx_rx 304. A logic one on sec_tx_rx 304 input activates ASK modulator 59. The data to be transmitted, sec_data_tx signal 305 can be inverted and then applied to AND gate input 276. AND gate output 277 can be either the clock signal on line 54a or a logic zero. In this configuration, an RF carrier can be transmitted when signal 305 is a logic zero.

While specific embodiments of practicing the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting to the scope of the invention which is to be given the full breadth of the following claims, and any and all embodiments thereof.

We claim:

1. An apparatus for transcutaneously providing a first power signal to and communication of a first and a second information signal with an implantable device, said apparatus comprising:
    a. an external unit including first power means for generating said first power signal, first signalling means for generating said first information signal, first receiving means for receiving said second information signal, and first coupling means connected to said first power means and said first signalling means and said first receiving means, said first coupling means for independently coupling said first power signal and said first information signal; and
    b. an internal unit including second power means for receiving said first power signal, second signalling means for generating said second information signal, second receiving means for receiving said first information signal, and second coupling means connected to said second power means and said second signalling means and said second receiving means for independently coupling said first power signal and said second information signal.

2. The apparatus of claim 1 wherein said first power means generates said power signal at a power frequency, said first signalling means generates said first information signal at a frequency greater than said power frequency, said second signalling means generates said second information signal at a frequency greater than said power frequency, and said frequency of said first signalling means being different from said frequency of said second signalling means.

3. The apparatus of claim 2 wherein said external unit comprises:
    a. a power converter for converting a power input signal at a first preselected frequency to said first power signal at said power frequency;
    b. an external coupler connected to said power converter and coupled to a common transmission channel for transmitting said power signal and for communicating said first and second information signals;
    c. an external signal conditioner interposed between said external coupler and said power converter for symmetrically transceiving said first and second information signals; and
    d. an external data controller connected to said external signal conditioner for symmetrically controlling said first and second information signals.

4. The apparatus of claim 3 wherein said external data controller further comprises first suppression means for suppressing deterministic noise in at least one of said first and second information signals.

5. The apparatus of claim 4 wherein said internal data controller further comprises second suppressing means for suppressing deterministic noise in at least one of said first and second information signals.

6. The apparatus of claim 2 wherein said internal unit comprises:
    an internal coupler coupled to a common transmission channel for receiving said first power signal and for communicating said first and second information signals;
    b. a voltage regulator connected between said internal coupler and said implantable device, said voltage regulator for converting said first power signal into a second power signal having a preselected current and providing said second power signal to said implantable device;
    c. an internal signal conditioner interposed between said internal coupler and said voltage regulator for symmetrically transceiving said first and second information signals; and
    d. an internal data controller connected between said internal signal conditioner and said implantable device, said internal data controller for symmetrically controlling said first and second information signals.

7. The apparatus of claim 6 wherein said internal data controller further comprises second suppression means for suppressing deterministic noise in at least one of said first and second information signals.

8. The apparatus of claim 6 wherein said voltage regulator further comprises shunting means for confining said power signal to said internal coupler when said preselected current is approximately zero amperes, said shunting means being synchronized to coincide with zero-crossings of said preselected current, so that switching losses and electromagnetic interference are minimized thereby.

9. The apparatus of claim 1 wherein said first power means transmits said power signal at a first power frequency, and said first and second signalling means generates said first and second information signal at a frequency greater than said first power frequency, said frequency of said first signalling means being approximately equal to said frequency of said second signalling means.

10. The apparatus of claim 3 wherein said external unit comprises:
   a. a power converter for converting a power input signal at a first preselected frequency to said first power signal at said power frequency;
   b. an external coupler connected to said power converter and coupled to a common transmission channel for transmitting said first power signal and for communicating said first and second information signals;
   c. an external signal conditioner interposed between said external coupler and said power converter for symmetrically transceiving said first and second information signals; and
   d. an external data controller connected to said external signal conditioner for symmetrically controlling said first and second information signals.

11. The apparatus of claim 9 wherein said internal unit comprises:
   a. an internal coupler coupled to a common transmission channel for receiving said first power signal and for communicating said first and second information signals;
   b. a voltage regulator connected between said internal coupler and said implantable device, said voltage regulator for converting said first power signal into a second power signal having a preselected current and providing said second power signal to said implantable device;
   c. an internal signal conditioner interposed between said internal coupler and said voltage regulator for symmetrically transceiving said first and second information signals; and
   d. an internal data controller connected between said internal signal conditioner and said implantable device, said controller for symmetrically controlling said first and second information signals.

12. The apparatus of claim 11 wherein said external unit comprises:
   a. a power converter for converting a power input signal at a first preselected frequency to said power signal at said power frequency;
   b. an external coupler connected to said power converter and coupled to said common transmission channel for transmitting said power signal and for communicating said first and second information signals;
   c. an external signal conditioner interposed between said external coupler and said power converter for symmetrically transceiving said first and second information signals; and
   d. an external data controller connected to said external signal conditioner for symmetrically controlling said first and second information signals.

13. The apparatus of claim 12 wherein said external coupler includes a primary tuned circuit and said internal coupler includes a secondary tuned circuit.

14. The apparatus of claim 13 wherein said primary and secondary tuned circuits have a resonant frequency.

15. The apparatus of claim 14 wherein said resonant frequency is about 160 kilohertz.

16. The apparatus of claim 12 wherein said first signal conditioner includes a first frequency-selective filter, and said second signal conditioner includes a second frequency-selective filter, each of said frequency-selective filters having an upper cutoff frequency and a lower cutoff frequency and a center frequency.

17. The apparatus of claim 16 wherein the respective lower and upper cutoff frequencies of said first and second frequency-selective filters are about 7.9 megahertz and about 8.1 megahertz, and the center frequency of said first and second frequency selective filters is about 8 megahertz.

18. The apparatus of claim 12 wherein said symmetrically controlling includes amplitude-shift-keying modulation of a data signal upon a radio-frequency carrier signal of a preselected carrier frequency.

19. The apparatus of claim 18 wherein said preselected carrier frequency is about 8 megahertz.

20. The apparatus of claim 12 wherein said first preselected frequency is about zero Hertz and said power input signal is a DC power input signal.

21. The apparatus of claim 12 wherein the first preselected frequency is about 60 Hertz and said power input signal is an AC power input signal.

22. The apparatus of claim 12 wherein said power frequency is about 160 kilohertz.

23. The apparatus of claim 12 wherein said external data controller further comprises first suppression means for suppressing deterministic noise in at least one of said first and second information signals.

24. The apparatus of claim 23 wherein said internal data controller further comprises second suppressing means for suppressing deterministic noise in at least one of said first and second information signals.

25. The apparatus of claim 11 wherein said internal data controller further comprises second suppression means for suppressing deterministic noise in at least one of said first and second information signals.

26. The apparatus of claim 11 wherein said voltage regulator further comprises shunting means for confining said power signal to said internal coupler when said preselected current is approximately zero amperes, said shunting means being synchronized to coincide with zero-crossings of said preselected current, so that switching losses and electromagnetic interference are minimized thereby.

27. An apparatus for transcutaneously providing a power signal to and communication of a first and a second information signals with an implantable device, said apparatus comprising:
   a. an external unit having
      i. a power converter for converting a power input signal at a first preselected frequency to a power signal at a power frequency;
      ii. an external coupler connected to said power converter and coupled to a common transmission channel for transmitting said power signal and for communicating said first and second information signals, said transmitting being independent of said communicating;
      iii. an external signal conditioner interposed between said external coupler and said power converter for symmetrically transceiving said first and second information signals; and
      iv. an external data controller connected to said external signal conditioner for symmetrically controlling said first and second information signals; and
   b. an internal unit having
      i. an internal coupler coupled to said common transmission channel for receiving said power signal and for communicating said first and second information signals, said receiving being independent of said communicating;
      ii. a voltage regulator connected between said internal coupler and said implantable device, said voltage regulator for converting said power signal into said second power signal and providing said second power signal to said implantable device;

iii. an internal signal conditioner interposed between said internal coupler and said voltage regulator for symmetrically transceiving said first and second information signals; and iv. an internal data controller connected between said internal signal conditioner and said implantable device, said controller for symmetrically controlling said first and second information signals.

28. The apparatus of claim 27 wherein said external coupler includes a primary tuned circuit and said internal coupler includes a secondary tuned circuit.

29. The apparatus of claim 27 wherein said first signal conditioner includes a first frequency-selective filter, and said second signal conditioner includes a second frequency-selective filter, each of said frequency-selective filters having an upper cutoff frequency and a lower frequency cutoff and a center frequency.

30. The apparatus of claim 29 wherein the respective lower and upper cutoff frequencies of said first and second frequency-selective filters are about 7.9 megaHertz and about 8.1 megahertz, and the center frequency of said first and second frequency selective filters is about 8 megahertz.

31. The apparatus of claim 27 wherein said symmetrically controlling includes amplitude-shift-keying modulation of a data signal upon a radio-frequency carrier signal of a preselected carrier frequency.

32. The apparatus of claim 31 wherein said preselected carrier frequency is about 8 megahertz.

33. The apparatus of claim 27 wherein said power frequency is about 160 kilohertz.

34. The apparatus of claim 27 wherein said primary and secondary tuned circuits have a resonant frequency.

35. The apparatus of claim 34 wherein said resonant frequency is about 160 kilohertz.

36. An apparatus for transcutaneously providing a power signal to and communication of a first and second information signals between an external control unit and an implantable device, said apparatus comprising:

a. an external unit having
   i. a power converter for receiving a power input signal and converting said power input signal at said first preselected frequency to said power signal at a power frequency;
   ii. an external coupler connected to said power converter and coupled to a common transmission channel, said external coupler for transmitting said signal and for communicating said first and second information signals, said transmitting being independent of said communicating;
   iii. an external signal conditioner interposed between said external coupler and said power converter for symmetrically transceiving said first and second information signals through said common transmission channel; and
   iv. an external data controller connected to said external signal conditioner for symmetrically controlling said first and second information signals, said external data controller having external link communicating said first and second information signals with said external control unit across said external link, said symmetrically controlling including modulation and demodulation of said first and second information signals according to a preselected modulation technique;

b. an internal unit having
   i. an internal coupler coupled to said common transmission channel for receiving said power signal, said internal coupler for receiving said power signal and for communicating said first and second information signals, said receiving being independent of said communicating;
   ii. a voltage regulator connected between said internal coupler and said implantable device, said voltage regulator for converting said power signal into said second power signal, said second power signal having a preselected current with a preselected voltage at a preselected frequency, said voltage regulator providing said second power signal to said implantable device;
   iii. an internal signal conditioner interposed between said internal coupler and said voltage regulator for symmetrically transceiving said first and second information signals through said common transmission channel; and
   iv. an internal data controller connected between said internal signal conditioner and said implantable device for symmetrically controlling said first and second information signals, said symmetrically controlling including modulation and demodulation of said first and second information signals according to said preselected modulation technique, said implantable device being in communication with said external control unit thereby; and c. said external coupler including a primary tuned circuit, said internal coupler including a secondary tuned circuit, said primary and secondary tuned circuits having a resonant frequency, said first signal conditioner including a first frequency-selective filter, said second signal conditioner including a second frequency-selective filter, each of said first and second frequency-selective filters having a cutoff frequencies and a center frequency, said preselected modulation technique including amplitude-shift-keying modulation of a data signal upon a radio-frequency carrier signal of a preselected carrier frequency, said center frequency being approximately equal to said preselected carrier frequency.

37. The apparatus of claim 36 wherein said power frequency is about 160 kilohertz.

38. The apparatus of claim 36 wherein said cutoff frequencies of said first and second frequency-selective filters is between about 7.9 megahertz and 8.1 megahertz, and said center frequency is about 8 megahertz.

39. The apparatus of claim 36 wherein said preselected carrier frequency is about 8 megahertz.

40. The apparatus of claim 36 wherein said resonant frequency is about 160 kilohertz.

41. The apparatus of claim 36 wherein said external data controller further comprises first suppression means for suppressing deterministic noise in at least one of said first and second information signals.

42. The apparatus of claim 41 wherein said internal data controller further comprises second suppressing means for suppressing deterministic noise in at least one of said first and second information signals.

43. The apparatus of claim 36 wherein said internal data controller further comprises second suppression means for suppressing deterministic noise in at least one of said first and second information signals.

44. The apparatus of claim 36 wherein said voltage regulator further comprises shunting means for confining said power signal to said internal coupler when said preselected current is approximately zero amperes, said shunting means being synchronized to coincide with zero-crossings of said preselected current, so that switching losses and electromagnetic interference are minimized thereby.

* * * * *